United States Patent
Dore et al.

(10) Patent No.: US 10,989,477 B2
(45) Date of Patent: Apr. 27, 2021

(54) APPARATUS AND METHOD FOR CONDUCTING HOT WORK

(71) Applicant: Safezone Safety Systems, LLC, Houma, LA (US)

(72) Inventors: David Allen Dore, Erath, LA (US); Robert C. Tucker, Baton Rouge, LA (US); Chad A. Grand, Baton Rouge, LA (US)

(73) Assignee: Safezone Safety Systems, LLC, Houma, LA (US)

( * ) Notice: Subject to any disclaimer, the term of this patent is extended or adjusted under 35 U.S.C. 154(b) by 1296 days.

(21) Appl. No.: 14/579,780

(22) Filed: Dec. 22, 2014

(65) Prior Publication Data
US 2015/0101396 A1    Apr. 16, 2015

Related U.S. Application Data

(63) Continuation of application No. 12/412,197, filed on Mar. 26, 2009, now Pat. No. 8,947,249.

(51) Int. Cl.
| | | |
|---|---|---|
| G08B 21/00 | (2006.01) | |
| F27D 21/04 | (2006.01) | |
| G01N 33/00 | (2006.01) | |
| G05B 9/05 | (2006.01) | |
| B23K 37/00 | (2006.01) | |

(52) U.S. Cl.
CPC ......... F27D 21/04 (2013.01); G01N 33/0057 (2013.01); G05B 9/05 (2013.01); B23K 37/006 (2013.01)

(58) Field of Classification Search
USPC .............. 340/506, 626, 632, 679, 691.6, 3.1
See application file for complete search history.

(56) References Cited

U.S. PATENT DOCUMENTS

| | | |
|---|---|---|
| 3,452,764 A | 7/1969 | Bell |
| 3,946,571 A | 3/1976 | Pate et al. |
| 4,068,975 A | 1/1978 | Eskeli |
| 4,249,463 A | 2/1981 | Hornby |

(Continued)

FOREIGN PATENT DOCUMENTS

| | | |
|---|---|---|
| GB | 2311847 A | 10/1997 |
| GB | 2382593 B | 6/2005 |

OTHER PUBLICATIONS

Casso, C.G. "Current Applications of Oil Well Logging Equipment in Hazardous Areas." Anadrill Schlumberger, USA, Electrical Safety in Hazardous Environments, Apr. 19-21, 1994, Conference Publication No. 390 @ IEE, 1994.

(Continued)

*Primary Examiner* — Hai Phan
*Assistant Examiner* — Son M Tang
(74) *Attorney, Agent, or Firm* — Roy Kiesel Ford Doody & North, APLC; Chad A. Grand

(57) ABSTRACT

In the specification and drawings, an apparatus for conducting hot work is described and shown with an enclosure; a hot work apparatus operable within the enclosure; and a detector located exterior of the enclosure, the detector being in detecting communication with the interior of the enclosure, such that the detector detects the presence of a condition within the enclosure. A method of conducting hot work is also described and shown.

6 Claims, 6 Drawing Sheets

(56) References Cited

U.S. PATENT DOCUMENTS

| | | | |
|---|---|---|---|
| 4,257,777 A * | 3/1981 | Dymond | G01N 21/766 422/52 |
| 4,297,940 A | 11/1981 | Hainline | |
| 4,560,873 A | 12/1985 | McGowan et al. | |
| 4,742,763 A | 5/1988 | Holter et al. | |
| 4,771,929 A | 9/1988 | Bahr et al. | |
| 4,968,975 A | 11/1990 | Fritz | |
| 5,026,219 A | 6/1991 | Wallace | |
| 5,101,604 A | 4/1992 | Wardlaw, III | |
| 5,176,566 A | 1/1993 | Crouch | |
| 5,497,573 A | 3/1996 | Stadjuhar et al. | |
| 5,550,375 A | 8/1996 | Peters et al. | |
| 5,552,775 A | 9/1996 | Harley | |
| 5,685,771 A | 11/1997 | Kleppen | |
| 5,702,296 A | 12/1997 | Grano | |
| 5,725,426 A | 3/1998 | Alvarez | |
| 6,060,689 A | 5/2000 | Wilson | |
| 6,076,313 A | 6/2000 | Pannell et al. | |
| 6,328,775 B1 | 12/2001 | Fuchs | |
| 6,402,613 B1 | 6/2002 | Teagle | |
| 6,540,603 B1 | 4/2003 | Koskinen | |
| 6,701,776 B2 | 3/2004 | Stetter | |
| 6,741,181 B2 | 5/2004 | Skaggs | |
| 6,783,054 B1 * | 8/2004 | Pregeant, Jr. | B23K 9/321 219/130.01 |
| 6,830,730 B2 * | 12/2004 | Rhodes | G01N 31/12 422/50 |
| 7,021,165 B2 | 4/2006 | Brunck et al. | |
| 7,022,993 B1 | 4/2006 | Williams, II et al. | |
| 7,091,848 B2 | 8/2006 | Albarado | |
| 7,094,142 B1 | 8/2006 | Maskell | |
| 7,193,501 B1 | 3/2007 | Albarado et al. | |
| 7,375,643 B2 | 5/2008 | McAward | |
| 7,397,361 B2 | 7/2008 | Paulsen | |
| 7,456,753 B2 | 11/2008 | Kitagawa et al. | |
| 7,504,962 B2 | 3/2009 | Smith | |
| 7,518,484 B2 | 4/2009 | Albarado et al. | |
| 7,765,072 B2 | 7/2010 | Eiler et al. | |
| 8,024,982 B2 | 9/2011 | Pettit et al. | |
| 2009/0134995 A1 | 5/2009 | Wardlaw, III | |
| 2011/0204032 A1 * | 8/2011 | Wardlaw | B23K 9/16 219/130.21 |

OTHER PUBLICATIONS

MMS Production Inspection Form Procedural Handbook (2000).
Browning, I.G. "Welding Hot Work Habitats" Society of Petroleum Engineers (1994).
Bebco Industries, Inc., Custom Metallic Enclosures Division Technical Bulletin-Design Guide & Specifications, CME-DGS-R1.0, Jan. 2000.
Bebco Industries, Inc., Modular Industrial Housing for Equipment & Personnel Brochure, 2004.
Bebco Industries, Inc. Industrial Duty Fiberglass Shelters for Highly Corrosive & Marine Locations ISD Technical Bulletin IDFS-R1.1, Jul. 2004.
Bebco Industries, Inc. Model RDP-24 Remote Mount Dual Blower Building Pressurization Unit, ECU Division Technical Bulletin RDP-24-R1.0, May 1997.
Bebco Industries, Inc. Model WDP-24 Wall Mount Dual Blower Building Pressurization Unit, ECU Division Technical Bulletin WDP-24-R1.0, May 1997.
Bebco Industries, Inc. Models GD & GDSB Gas Detector Sensors, Monitors, Power Supplies & Mounting Brackets, ECU Division Technical Bulletin GDA-R1.0, May 1997.
Kidden Fenwal, AnaLaser, HSSD®-LTT (High Sensitivity Smoke Detection System Laser Technology Type), Jun. 1992, 89.58.2.

* cited by examiner

APPARATUS AND METHOD FOR CONDUCTING HOT WORK

I. CROSS REFERENCE TO RELATED APPLICATION

This application is a continuation of U.S. application Ser. No. 12/412,197 filed on Mar. 26, 2009, which is incorporated by reference herein in its entirety.

II. BACKGROUND

A. Technical Field

An embodiment described herein is an apparatus and method for conducting hot work.

B. Background Art

An embodiment of an apparatus and method for conducting hot work is described in U.S. Pat. No. 6,783,054 to Pregeant, Jr. et al., U.S. Pat. No. 7,397,361 to Paulsen, U.S. Pat. No. 7,091,848 to Albarado, and U.S. Pat. No. 7,193,501 to Albarado, et al., each of which are hereby incorporated by reference.

III. BRIEF SUMMARY

An embodiment can be an apparatus for conducting hot work comprising: an enclosure; a hot work apparatus operable within the enclosure; and a detector located exterior of the enclosure, the detector being in detecting communication with the interior of the enclosure, such that the detector detects the presence of a condition within the enclosure.

An embodiment can be an apparatus wherein the hot work apparatus is shut down in response to the detector detecting the presence of a predetermined condition within the enclosure.

An embodiment can be an apparatus further comprising a housing located adjacent to the enclosure, the interior of the housing being fluidly connected to the interior of the enclosure, the detector being fluidly connected to the interior of the housing.

An embodiment can be an apparatus further comprising a gap between the housing and the enclosure.

An embodiment can be an apparatus wherein the housing is not in contact with the enclosure.

An embodiment can be an apparatus wherein the housing is portable.

An embodiment can be an apparatus further comprising a stand attached to the housing.

An embodiment can be an apparatus further comprising a damper attached to the housing.

An embodiment can be an apparatus wherein the detector comprises a first combustible gas detector.

An embodiment can be an apparatus further comprising: an oxygen detector fluidly connected to the interior of the housing; and a pressure detector fluidly connected to the interior of the housing.

An embodiment can be an apparatus wherein at least one of the first combustible gas detector, the oxygen detector and the pressure detector is located exterior of the housing.

An embodiment can be an apparatus further comprising: a blower assembly in fluid communication with the interior of the enclosure; a second combustible gas detector located so as to detect the presence of a combustible gas in or near to an air intake of the blower assembly; a manual shutdown switch located within the enclosure; and a controller in communication with the first combustible gas detector, the second combustible gas detector, the oxygen detector, the pressure detector and the manual shutdown switch, the controller being in communication with the hot work apparatus and capable of controlling the operation of the hot work apparatus in response to a signal received from at least one of the first combustible gas detector, the second combustible gas detector, the oxygen detector, the pressure detector and the manual shutdown switch.

An embodiment can be an apparatus wherein the hot work apparatus comprises a welding apparatus.

An embodiment can be an apparatus further comprising an aperture extending from the interior of the enclosure to the exterior of the enclosure, the detector being fluidly connected to the interior of the enclosure through the aperture.

An embodiment can be an apparatus further comprising a conduit between the aperture and the detector.

An embodiment can be an apparatus further comprising a blower assembly in fluid communication with the interior of the enclosure.

An embodiment can be an apparatus further comprising a positive pressure atmosphere within the enclosure.

An embodiment can be an apparatus further comprising a second detector for detecting a condition exterior the enclosure.

An embodiment can be an apparatus wherein the detector comprises a combustible gas detector.

An embodiment can be an apparatus wherein the combustible gas detector is fluidly connected to the interior of the enclosure.

An embodiment can be an apparatus wherein the combustible gas detector is in light communication with the interior of the enclosure.

An embodiment can be an apparatus wherein the combustible gas detector is in infrared light communication with the interior of the enclosure.

An embodiment can be an apparatus wherein the combustible gas detector is in light communication with air transferred from the interior of the enclosure to the exterior of the enclosure.

An embodiment can be an apparatus wherein the combustible gas detector is in infrared light communication with air transferred from the interior of the enclosure to the exterior of the enclosure.

An embodiment can be an apparatus for conducting hot work comprising: an enclosure; a blower assembly in fluid communication with the interior of the enclosure; and a means for detecting the presence of combustible gas that is within the enclosure by sampling air that is not within the enclosure.

An embodiment can be an apparatus wherein the air that is not within the enclosure has been transferred from the interior of the enclosure.

An embodiment can be an apparatus further comprising a welding apparatus operable within the enclosure.

An embodiment can be an apparatus further comprising a positive pressure atmosphere within the enclosure.

An embodiment can be an apparatus wherein the means for detecting the presence of combustible gas that is within the enclosure by sampling air that is not within the enclosure comprises a combustible gas detector located exterior of the enclosure.

An embodiment can be an apparatus for conducting hot work comprising: an enclosure; a first combustible gas detector for detecting combustible gas within the enclosure; an oxygen detector for detecting oxygen within the enclosure; and a pressure detector for detecting pressure within the enclosure, at least one of the first combustible gas detector, the oxygen detector and the pressure detector being located exterior of the enclosure.

An embodiment can be an apparatus further comprising: a blower assembly in fluid communication with the interior of the enclosure; a second combustible gas detector located so as to detect the presence of a combustible gas in or near to an air intake of the blower assembly; a welding apparatus operable with the enclosure, the operation of the welding apparatus being controllable in response to a signal generated by at least one of the first combustible gas detector, the second combustible gas detector, the oxygen detector and the pressure detector.

An embodiment can be an apparatus for conducting hot work comprising: an enclosure; a welding apparatus operable at least partially within the enclosure; a blower assembly in fluid communication with the interior of the enclosure; a manual shutdown switch in communication with the welding apparatus; an oxygen detector fluidly connected to the interior of the enclosure and in communication with the welding apparatus; a pressure detector fluidly connected to the interior of the enclosure and in communication with the welding apparatus; and a combustible gas detector located exterior of the enclosure, the combustible gas detector being fluidly connected to the interior of the enclosure such that the combustible gas detector detects the presence of a combustible gas within the enclosure, the combustible gas detector being in communication with the welding apparatus.

An embodiment can be an apparatus wherein the welding apparatus is shut down in response to a signal generated by at least one of the oxygen detector, the pressure detector and the combustible gas detector.

An embodiment can be a method of terminating hot work within an enclosure comprising: conducting hot work within an enclosure; transferring air from the interior of the enclosure to the exterior of the enclosure; sampling the air transferred from the interior of the enclosure for the presence of combustible gas; and terminating the hot work within the enclosure in response to detection of a level of combustible gas in the air transferred from the interior of the enclosure to the exterior of the enclosure.

An embodiment can be a method further comprising producing a positive pressure atmosphere within the enclosure.

An embodiment can be a method wherein producing a positive pressure atmosphere within the enclosure further comprises transferring air from the exterior of the enclosure to the interior of the enclosure.

An embodiment can be a method wherein terminating hot work within the enclosure in response to detection of a level of combustible gas in the air transferred from the interior of the enclosure further comprises terminating hot work within the enclosure in response to detection of a level of combustible gas above a predefined level.

An embodiment can be a method wherein the predefined level is at most 25% of the lower explosive limit of the combustible gas.

An embodiment can be a method further comprising forming the enclosure at a location where hot work is to be conducted on a production platform that drills for flammable materials.

An embodiment can be a method further comprising: conducting drilling operations for flammable materials on the production platform; and terminating drilling operations in response to detection of a level of combustible gas in the air transferred from the interior of the enclosure.

An embodiment can be a method further comprising sampling the air transferred from the interior of the enclosure for the presence of a level of oxygen.

An embodiment can be a method wherein the conducting hot work within an enclosure further comprises conducting welding within the enclosure.

An embodiment can be a method of detecting a combustible gas entering an enclosure by detecting a pressure drop in the atmosphere within the enclosure comprising: transferring air from the exterior of the enclosure to the interior of the enclosure; detecting a level of combustible gas in or near to a source of the air transferred from the exterior of the enclosure to the interior of the enclosure; stopping the transferring of air from the exterior of the enclosure to the interior of the enclosure in response to the detecting a level of combustible gas; and detecting a pressure drop in the atmosphere within the enclosure so as to detect a combustible gas entering the enclosure.

An embodiment can be a method further comprising conducting hot work in the enclosure.

An embodiment can be a method further comprising terminating the hot work in the enclosure in response to the detecting a pressure drop in the atmosphere within the enclosure.

An embodiment can be a method further comprising transmitting a signal to a controller in response to the detecting a pressure drop in the atmosphere within the enclosure.

An embodiment can be a method further comprising transmitting a signal from a controller to a power source of the hot work.

An embodiment can be a method wherein terminating the hot work further comprises terminating the hot work in response to a signal from the controller.

An embodiment can be an apparatus for conducting hot work comprising: an enclosure; a hot work apparatus operable within the enclosure; a blower assembly in fluid communication with the interior of the enclosure; and a detector located so as to detect the presence of a condition in or near to an air intake of the blower assembly, the detector being in communication with the blower assembly, the detector being isolated from the hot work apparatus.

An embodiment can be an apparatus further comprising a first controller, the first controller being in communication with the hot work apparatus, the first controller being isolated from the blower assembly.

An embodiment can be an apparatus further comprising a pressure detector fluidly connected to the interior of the enclosure, the pressure detector being in communication with the hot work apparatus.

An embodiment can be an apparatus wherein the pressure detector is isolated from the blower assembly.

An embodiment can be an apparatus further comprising a second controller, the second controller being in communication with the blower assembly, the second controller being in communication with the detector.

An embodiment can be an apparatus further comprising: a first controller, the first controller being in communication with the hot work apparatus, the first controller being isolated from the blower assembly; and a pressure detector fluidly connected to the interior of the enclosure, the pressure detector being in communication with the first controller.

An embodiment can be an apparatus wherein the detector comprises a combustible gas detector located so as to detect the presence of a level of combustible gas in or near to an air intake of the blower assembly.

An embodiment can be an apparatus further comprising: an oxygen detector located so as to detect the presence of a level of oxygen in or near to an air intake of the blower assembly, the oxygen detector being in communication with the blower assembly, the oxygen detector being isolated from the hot work apparatus; and a carbon monoxide detector located so as to detect the presence of a level of carbon monoxide in or near to an air intake of the blower assembly, the carbon monoxide detector being in communication with the blower assembly, the carbon monoxide detector being isolated from the hot work apparatus.

The above summary is not intended to describe each illustrated embodiment or every possible implementation. The figures and the detailed description which follow exemplify these embodiments.

IV. BRIEF DESCRIPTION OF THE SEVERAL VIEWS OF THE DRAWINGS

V. DETAILED DESCRIPTION OF THE EMBODIMENTS DEPICTED IN THE DRAWINGS

Figure 1:
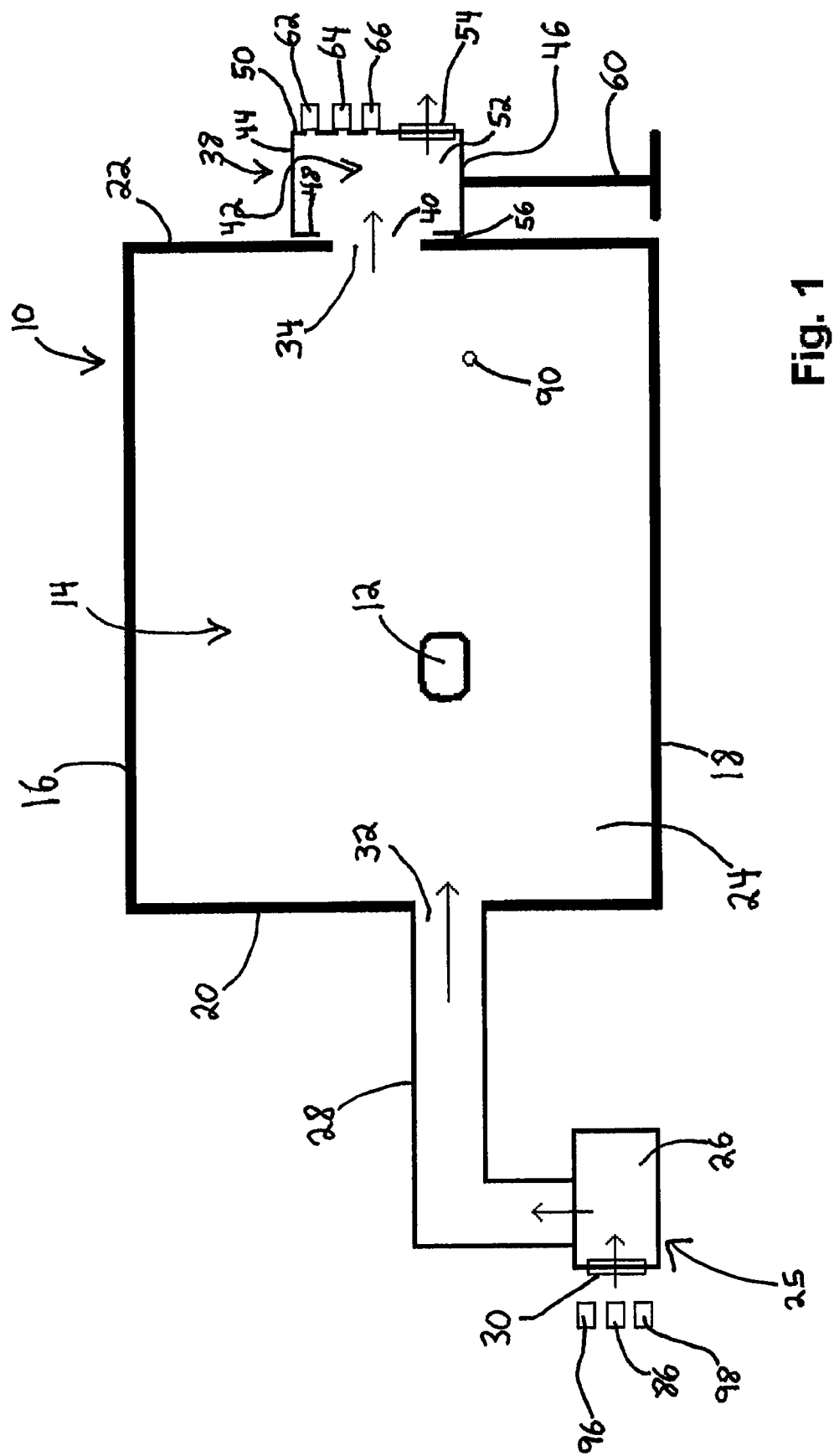
FIG. 1 is a side section view of an embodiment described herein.

As shown in the accompanying drawings, an embodiment is an apparatus and method for conducting hot work. As shown in FIG. 1, an embodiment can have an enclosure 10. The enclosure 10 can have a plurality of sides that define the interior 14 of the enclosure 10 and surround a hot work apparatus 12 that is operable within the interior 14 of the enclosure 10. The sides of the enclosure 10 can include ceiling 16, floor 18, left wall 20, right wall 22, rear wall 24 and a front wall (not shown). The sides of the enclosure 10 can be made of materials such as wood, flame resistant plywood, fabric, metal, fiberglass, and/or any other suitable materials. In an embodiment, sides, such as the floor and/or walls, can be flame resistant plywood that is lined on the interior side with sheet metal, such as aluminum or steel sheet metal. As opposed to or in addition to sheet metal, the sides can be lined with one or more welding blankets. In an embodiment, the floor and a portion of the walls beginning at the floor and extending upwards about six inches can be lined with one or more welding blankets. An example of a welding blanket is sold as item number CF16 under the trademark PANTHERFELT. In an embodiment, the enclosure 10 can be formed at locations such as a work site, a petroleum plant, a chemical plant, a pipeline and/or a production platform. In an embodiment, a production platform can be a drilling rig that drills for flammable materials, such as a drilling platform that drills into the earth for hydrocarbons. The enclosure 10 can also be formed at other locations, such as any location where it could be desirable to permanently or temporarily isolate hot work within the enclosure 10. A scaffolding framework can be formed around the enclosure 10 such that the scaffolding framework provides support for the enclosure 10 and secures the position of the enclosure 10. The scaffolding framework can be made of materials such as wood, metal, plastic or any other suitable materials. In an embodiment, the scaffolding framework can be made of fire retardant wooden two-by-fours and/or conventional metal scaffolding.

In an embodiment, the enclosure 10 can be formed adjacent to flammable materials, such as hydrocarbons contained in tanks, pipes or other structures. Hot work can be conducted within the enclosure so that the hot work is isolated from the flammable materials. Hot work is work that produces a source of ignition, such as arcs, sparks or flames. The hot work can be conducted within the enclosure 10 by apparatus such as an arc welder, mig welder, tig welder, cutting torch, grinder, analyzing equipment, spectrometer and/or other apparatuses which can produce a source of ignition.

The sides of the enclosure 10 can have openings that allow objects, such as pipes, decking, cables or other objects to pass through the sides of the enclosure 10. The openings can be formed by cutting the opening into a side of the enclosure 10 when the enclosure 10 is being formed, or by forming the sides of the enclosure around such objects. Any remaining gaps between the sides of the enclosure 10 and the object can be sealed with a material such as fire resistant caulk or metal tape.

In an embodiment, a positive pressure atmosphere is within the enclosure 10. The positive pressure atmosphere can be produced within the enclosure 10 by transferring air from the exterior of the enclosure 10 to the interior 14 of the enclosure 10. In the embodiments depicted in FIGS. 1, 2 and 3, air is transferred from the exterior of the enclosure 10 to the interior 14 of the enclosure 10 by a blower assembly 25 (shown in schematic in FIGS. 4, 5 and 6), which can include blower 26. The blower 26 can be any device that is capable of producing a flow of air, such as a fan, a ducted fan, a compressed air source, such as an air compressor and/or a compressed air tank, an air pump and/or any other suitable device. In an embodiment, the blower 26 can be an electric, hydraulic or pneumatic blower. An example of a blower is an Air MAX-12, produced by COPPUS. In the embodiments depicted in FIGS. 1, 2 and 3, the blower 26 is in fluid communication with the interior of the enclosure 10 by way of duct 28. An air intake 30 of the blower 26 can be located at an area believed to be free of combustible gases, such as unclassified area of a drilling platform. In operation, air is transferred from the exterior of the enclosure 10 to the interior 14 of the enclosure 10 by passing through air intake 30 traveling through duct 28 and into the enclosure 10 at inlet aperture 32.

Referring to the embodiment depicted in FIG. 1, a positive pressure atmosphere within the enclosure 10 can cause air to be transferred from the interior 14 of the enclosure 10 to the exterior of the enclosure 10 by passing through an aperture, such as outlet aperture 34, which extends from the interior 14 of the enclosure 10 to the exterior of the enclosure 10. As shown in the embodiment depicted in FIGS. 1 and 3, the outlet aperture 34 can be approximately the same size as inlet aperture 32. In an embodiment, the outlet aperture 34 can be larger or smaller than the inlet aperture 32. As shown in the embodiment depicted in FIG. 3, a grill 36, such as a spark arresting filter, can be placed across outlet aperture 34. In an embodiment, the spark arresting filter can include a Flame Gard 1 produced by FLAME GARD. The grill 36 can hamper or prevent sources of ignition, such as sparks that can be created by hot work, from passing through the outlet aperture 34. One or more grills can also be placed across other apertures that may exist in the sides of the enclosure 10 or the housing 38.

Referring to the embodiment depicted in FIG. 1, a housing 38 can be located adjacent to the enclosure 10. The housing 38 can have a plurality of housing sides that define the interior 42 of the housing 38. The housing sides of the housing 38 can include housing ceiling 44, housing floor 46, housing left wall 48, housing right wall 50, housing rear wall 52 and a housing front wall (not shown). A housing side of housing 38 can have an aperture, such as a housing inlet aperture 40, located adjacent to outlet aperture 34 so as to allow a fluid connection between the interior 14 of the enclosure 10 and the interior 42 of the housing 38. The housing inlet aperture 40 can be approximately the same size as the outlet aperture 34 of the enclosure. The housing inlet aperture 40 can also be larger (see FIG. 1) or smaller than the outlet aperture 34. Housing 38 can also have a damper 54 attached to the housing 38. The damper 54 can provide an aperture that allows air to be transferred from the interior 42 of the housing 38 to the exterior of the housing 38 by passing through damper 54. The damper 54 can be a device such as a louver or valve and can have adjustable vents that can allow the flow of air through the damper 54 to be regulated. Air transferred from the interior 14 of the enclosure 10 to the interior 42 of the housing 38 can create a positive pressure atmosphere within the housing 38. The pressure level of a positive pressure atmosphere within the enclosure 10 and the housing 38 can be regulated or partially regulated by adjusting the vents of the damper 54. For example, to increase the pressure level of the positive pressure atmosphere within the enclosure 10 and the housing 38, the vents of the damper 54 could be closed or partially closed. To decrease the pressure level of the positive pressure atmosphere within the enclosure 10 and the housing 38, the vents of the damper 54 could be opened or partially opened. In an embodiment, the damper 54 can include a grill, such as a spark arresting filter. In the embodiment depicted in FIGS. 1 and 3, although some air may spill out of gap 56 between the housing 38 and the enclosure 10, adjusting the vents of the damper 54 can still have an effect on the pressure level of the positive pressure atmosphere within the enclosure 10 when the housing inlet aperture 40 is placed sufficiently near the outlet aperture 34 of the enclosure 10.

In an embodiment the positive pressure atmosphere within the enclosure 10 causes air to be transferred from the interior 14 of the enclosure 10 to the exterior of the enclosure 10 and into the interior 42 of the housing 38, and then from the interior 42 of the housing 38 to the exterior of the housing 38. In an embodiment, an air moving device, such as a fan, can be positioned at a location such as in or adjacent to outlet aperture 34, housing inlet aperture 40, conduit 58 (discussed below) and/or damper 54. The air moving device can cause air to be transferred from the interior 14 of the enclosure 10 to the exterior of the enclosure 10 and into the interior 42 of the housing 38, and then from the interior 42 of the housing 38 to the exterior of the housing 38.

Figure 2:
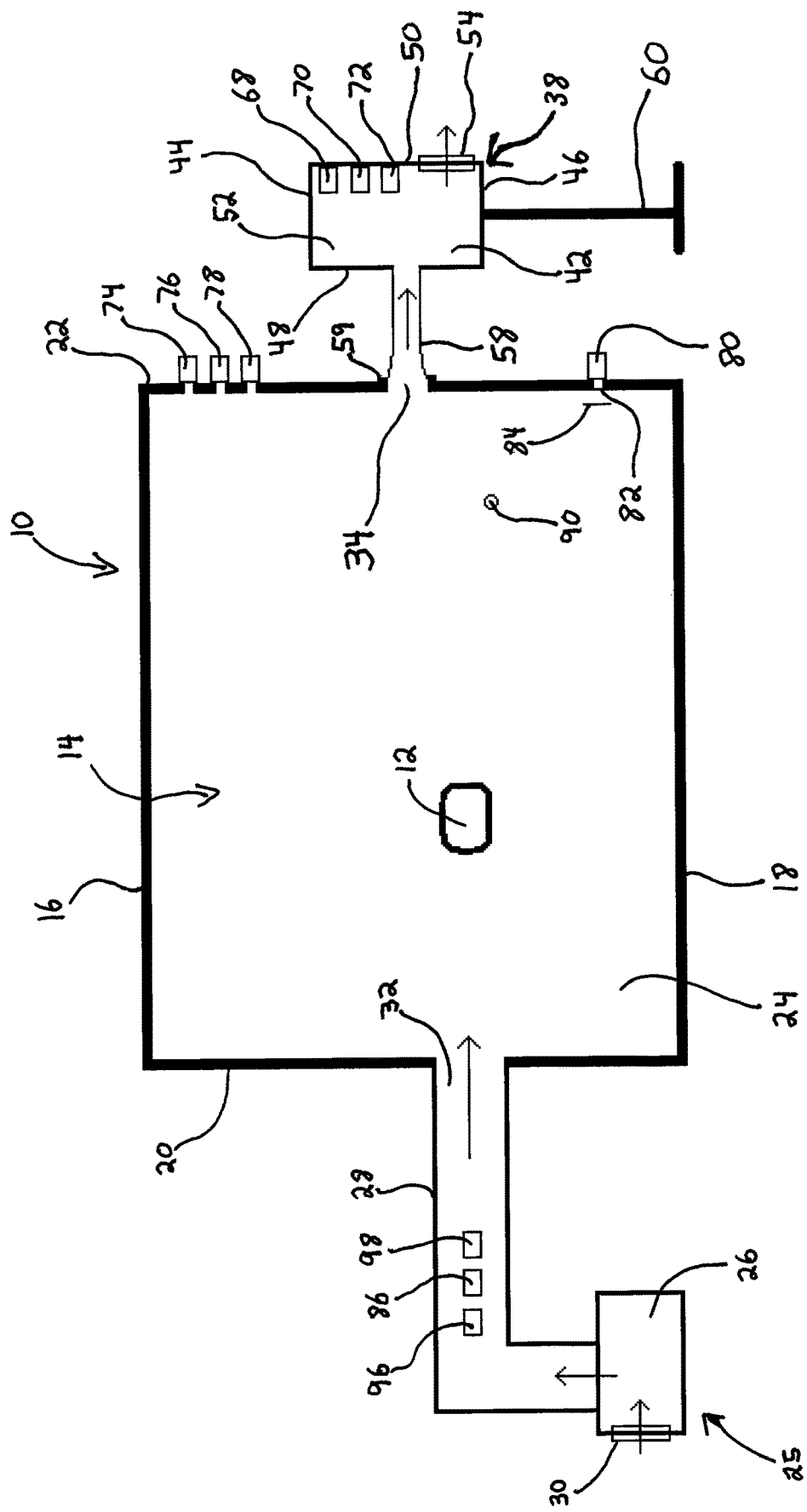
FIG. 2 is a side section view of an embodiment described herein.
Figure 3:
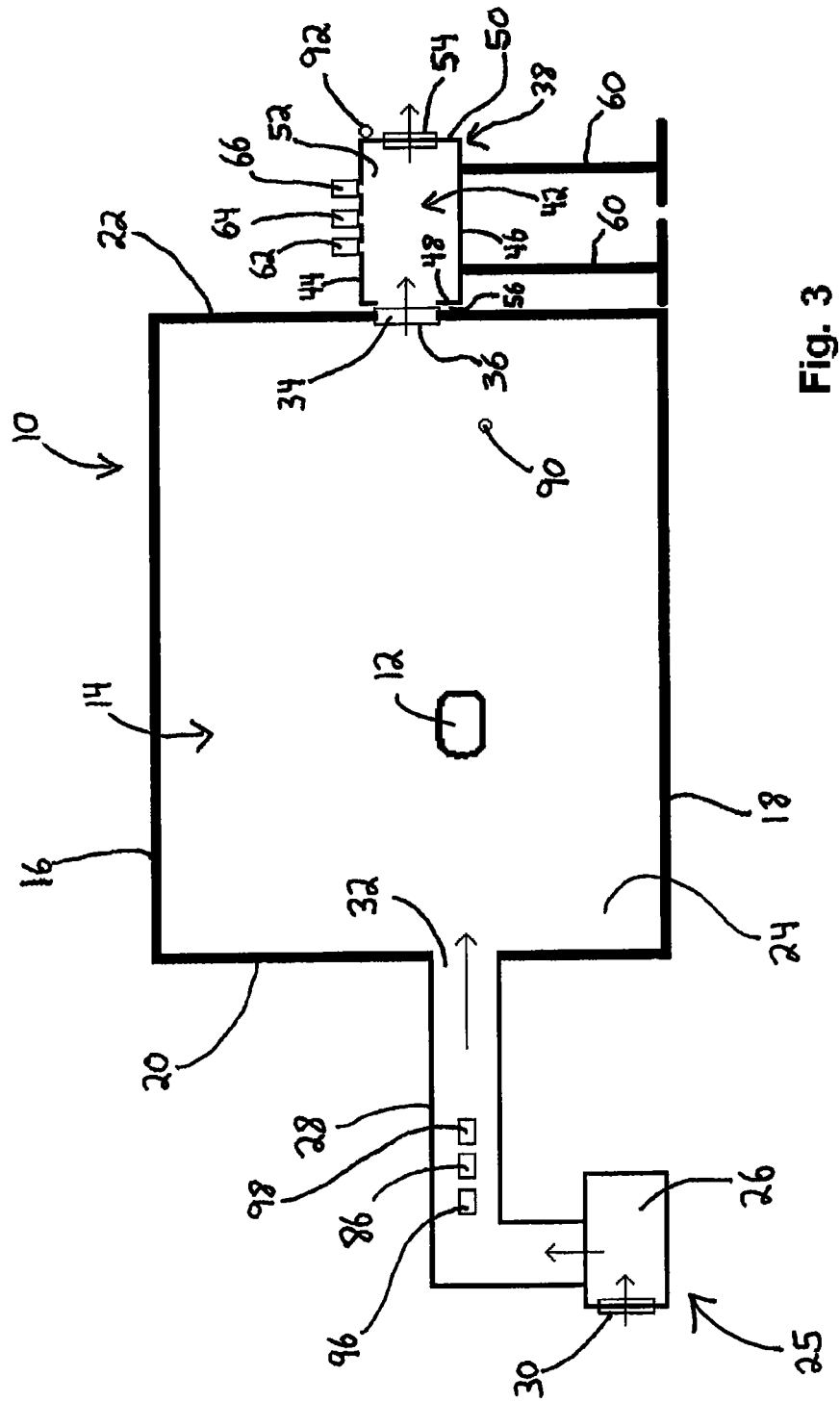
FIG. 3 is a side section view of an embodiment described herein.

Referring to the embodiments depicted in FIGS. 1 and 3, the housing 38 is not in contact with the enclosure 10 and can have a gap 56 between the housing 38 and the enclosure 10. In the embodiment depicted in FIG. 2, a conduit 58, such as ductwork, tubing or pipe, connects the housing 38 to the enclosure 10. The conduit 58 can be connected to the enclosure 10 by any means in the art. For example, as shown in FIG. 2, a flange 59 can connect the conduit 58 to an exterior of a wall of the enclosure 10. Referring to the embodiments depicted in FIGS. 1, 2 and 3, a stand 60 is attached to the housing 38. The stand 60 can be placed on a foundation, such as a deck of a drilling platform. The stand 60 can also be secured to the foundation which can increase stability. The housing 38 can be portable and can be moved to different locations that can be adjacent to an aperture in the sides of the enclosure 10. For example, an aperture can be drilled, cut or otherwise formed in a side of the enclosure 10 at a location so as to position a hot work apparatus 12 that is operable within the enclosure 10, generally in a line between inlet aperture 32 and outlet aperture 34. The housing 38 can then be placed so that housing inlet aperture 40 is adjacent to outlet aperture 34. If the location of the hot work within the enclosure 10 is changed, a new aperture can be formed in a side of the enclosure 10 at a location so as to position the hot work generally in a line between inlet aperture 32 and the newly formed aperture. The housing 38 can then be moved and placed in a location so that housing inlet aperture 40 is adjacent to the newly formed aperture. The housing 38 can also be moved to different locations on a drilling platform or different work sites.

Referring to the embodiments depicted in FIGS. 1, 2 and 3, detectors 62, 64, 66, 68, 70, 72, 74, 76, 78 and 80 are located exterior of the enclosure 10. Detectors 62, 64, 66, 68, 70, 72, 74, 76, 78 and 80 are in detecting communication with the interior 14 of the enclosure 10, such that the detectors detect the presence of a condition within the enclosure 10. In an embodiment, the presence of a condition can include detecting conditions such as a level of toxic gas, a level of combustible gas, a level of oxygen, a level of carbon monoxide, a level of hydrogen sulfide and/or other gases. The presence of a condition can also include detecting conditions such as a level of pressure, humidity, temperature and/or any other condition. As an example, the detectors can be mechanical, solid-state, chemical, electrochemical, electric, optical, infrared, photoionization, catalytic bead and/or any other type of detector. Depending on the detectors selected, the detectors can perform the detection function in various ways, for example by air sampling, pressure sensing, light absorption or any other way.

In the embodiments depicted in FIGS. 1 and 3, detectors 62, 64 and 66 are located exterior of the enclosure 10 and exterior of the housing 38, and are in detecting communication with the interior 14 of the enclosure 10 by being fluidly connected to the interior 14 of the enclosure 10. Detectors 62, 64 and 66 are fluidly connected to the interior 14 of the enclosure 10 by being fluidly connected to the interior 42 of the housing 38, which is itself fluidly connected to the interior 14 of the enclosure 10. In the embodiment depicted in FIG. 2, detectors 68, 70 and 72 are located exterior of the enclosure 10 and within the interior 42 of the housing 38, and are in detecting communication with the interior 14 of the enclosure 10 by being fluidly connected to the interior 14 of the enclosure 10. Detectors 68, 70 and 72 are fluidly connected to the interior 14 of the enclosure 10 by being fluidly connected to the interior 42 of the housing 38, which is itself fluidly connected to the interior 14 of the enclosure 10. Still referring to the embodiment depicted in FIG. 2, detectors 74, 76 and 78 are located exterior of the enclosure 10 and are attached to the exterior side of right wall 22, and are in detecting communication with the interior 14 of the enclosure 10 by being fluidly connected to the interior 14 of the enclosure 10 through apertures in right wall 22. Detector 80 is attached to the exterior side of right wall 22 and is in detecting communication with the interior 14 of the enclosure 10 by being in light communication with the interior 14 of the enclosure 10 through a glass window 82 in right wall 22.

Referring to the embodiments depicted in FIGS. 1, 2 and 3, detectors 62, 68, 74 and 80 can be combustible gas detectors. In an embodiment, a combustible gas detector can be any device that is capable of detecting combustible gas. An example of a combustible gas detector is a matched pair catalytic bead detector, such as model number FP-524C produced by DETCON Incorporated. The combustible gas detectors can detect the presence of combustible gases, such as fuel gases and/or hydrocarbon gases. Combustible gas detectors 62, 68 and 74 can be fluidly connected to the interior 14 of the enclosure 10 and can sample air transferred from the interior 14 of the enclosure 10 to the exterior of the enclosure 10 for the presence of combustible gas. By sampling air transferred from the interior 14 of the enclosure 10 to the exterior of the enclosure 10, the combustible gas detector can detect the presence of combustible gas within the enclosure 10. Another combustible gas detector 86 can be located so as to detect the presence of a combustible gas in or near to the air intake 30 of the blower 26. As used herein, a detector, such as combustible gas detector 86, is located so as to detect the presence of a condition, such as combustible gas, near to the air intake 30 of the blower 26 if the detector is capable of detecting a condition that is more likely than not to be transferred into the air intake 30 of the blower 26.

Referring to FIG. 2, detector 80 can be an infrared detector, such as an infrared combustible gas detector. An example of an infrared combustible gas detector is produced by DETCON Inc. under the model number IR-622. An infrared combustible gas detector 80 can be located exterior of the enclosure 10 and can transmit infrared light into the interior 14 of the enclosure 10, such as through a glass window 82 formed in a side of the enclosure 10. A mirror 84 can be placed within the enclosure 10 such that light transmitted by the infrared combustible gas detector 80 can reflect off of the mirror 84 and return to the infrared combustible gas detector 80. Since combustible gases such as combustible hydrocarbon gases can have different infrared absorption spectra, the infrared combustible gas detector can analyze the reflected infrared light to detect the presence of combustible hydrocarbon gas within the enclosure 10. In an embodiment, an infrared combustible gas detector can be located in or adjacent to housing 38 so as to be in infrared light communication with air transferred from the interior 14 of the enclosure 10 to the exterior of the enclosure 10. By sampling air transferred from the interior 14 of the enclosure 10 to the exterior of the enclosure 10, the infrared combustible gas detector can detect the presence of combustible gas within the enclosure 10.

Referring still to the embodiments depicted in FIGS. 1, 2 and 3, detectors 64, 70, and 76 can be oxygen detectors and/or carbon monoxide detectors. In an embodiment, the oxygen detectors and/or carbon monoxide detectors can be any device that is capable of detecting oxygen and/or carbon monoxide. An example of an oxygen detector is a galvanic metal air battery detector, such as model number DM-534 produced by DETCON Incorporated. An example of a carbon monoxide detector is an electrochemical fuel cell detector, such as model number DM-500IS-CO produced by DETCON Incorporated. Oxygen and/or carbon monoxide detectors 64, 70 and 76 can be fluidly connected to the interior 14 of the enclosure 10 and can sample air transferred from the interior 14 of the enclosure 10 to the exterior of the enclosure 10. By sampling air transferred from the interior 14 of the enclosure 10 to the exterior of the enclosure 10, the oxygen and/or carbon monoxide detectors can detect the presence of oxygen and/or carbon monoxide within the enclosure 10.

Referring still to the embodiments depicted in FIGS. 1, 2 and 3, detectors 66, 72 and 78 can be pressure detectors. The pressure detectors can be any device that is capable of detecting pressure and/or a change in pressure. An example of pressure detector is model number 616D produced by DWYER. Pressure detectors 64, 70 and 76 can be fluidly connected to the interior 14 of the enclosure 10 and can detect a level of pressure in the atmosphere within the interior 14 of the enclosure 10 and/or a pressure drop in the atmosphere within the interior 14 of the enclosure 10. Since pressure detectors 66 and 72 are fluidly connected to the interior 14 of the enclosure 10 by being fluidly connected to the interior 42 of the housing 38, pressure detectors 66 and 72 can detect a level of pressure in the atmosphere within the enclosure 10 and/or a pressure drop in the atmosphere within the enclosure 10 by detecting a level of pressure in the atmosphere within the housing 38 and/or a pressure drop in the atmosphere within the housing 38.

In an embodiment, one or more detectors can be located so as to detect the presence of a condition in or near to the air intake 30 of the blower 26. In the embodiments depicted in FIGS. 1, 2 and 3, detector 86 can be a combustible gas detector, detector 96 can be a carbon monoxide detector and detector 98 can be an oxygen detector. In an embodiment, a combustible gas detector, an oxygen detector, a carbon monoxide detector and a hydrogen sulfide detector can be located so as to detect the presence of a condition in or near to the air intake 30 of the blower 26; in addition, an oxygen detector, a carbon monoxide detector, a hydrogen sulfide detector and a pressure detector can be in detecting communication with the interior 14 of the enclosure 10.

Referring to the embodiments depicted in FIGS. 1, 2 and 3, each of detectors 62, 64, 66, 68, 70, 72, 74, 76, 78, 80, 86, 96 and 98 are located exterior of the enclosure 10. In another embodiment, one or more, or each of detectors 62, 64, 66, 68, 70, 72, 74, 76, 78, 80, 86, 96 and 98, can be located within the interior 14 of the enclosure 10. It should also be understood that the conditions detected and the detectors, including the number and/or type of detectors described herein, are exemplary of numerous conditions, detectors and configurations that may fall within the scope of the appended claims.

One or more of detectors 62, 64, 66, 68, 70, 72, 74, 76, 78, 80, 86, 96 and 98 can be in communication, such as wired or wireless communication, with a hot work apparatus 12, such as a power source of the hot work apparatus. In response to one or more of detectors 62, 64, 66, 68, 70, 72, 74, 76, 78, 80, 86, 96 and 98 detecting the presence of a condition, the detector can generate a signal that is transmitted to the hot work apparatus so as to terminate the hot work and/or cause the hot work apparatus to shut down. For example, the detectors can generate a signal in response to detecting the presence of a predetermined condition, such as a predefined level of oxygen, combustible gas, carbon monoxide, hydrogen sulfide, pressure and/or other conditions. In an embodiment a predefined level of oxygen can be a trace amount of oxygen that is at or near the detection capabilities of the detector. In another embodiment, the predefined level of oxygen can be a level of oxygen below 19.5% and/or above 23.5%.

As an additional example, detectors 62, 68 and 74 can generate a signal that is capable of terminating hot work within the enclosure in response to detecting the presence of a predetermined condition, such as a predefined level of combustible gas in the air transferred from the interior 14 of the enclosure 10 to the exterior of the enclosure 10. In an embodiment, the predefined level of combustible gas can be a trace amount of combustible gas that is at or near the detection capabilities of the detector. In another embodiment, the predefined level of combustible gas can be a percentage of the lower explosive limit of the combustible gas. The predefined level can be percentages such as 5%, 10%, 15%, 20% or 25% of the lower explosive limit of the combustible gas. The lower explosive limit (also known as the lower flammable limit) is the leanest percentage of combustible gas mixed with air that is explosive. Examples of possible lower explosive limits of some gases are provided in the following chart:

| GAS | "Lower Explosive or Flammable Limit" (LEL/LFL)/(%) |
|---|---|
| Acetaldehyde | 4 |
| Acetone | 2.6 |
| Acetylene | 2.5 |
| Ammonia | 15 |
| Arsine | 5.1 |
| Benzene | 1.35 |
| n-Butane | 1.86 |
| iso-Butane | 1.80 |
| iso-Butene | 1.8 |
| Butylene | 1.98 |
| Carbon Disulfide | 1.3 |
| Carbon Monoxide | 12 |
| Cyclohexane | 1.3 |
| Cycloproprane | 2.4 |
| Diethyl Ether | 1.9 |
| Ethane | 3 |
| Ethylene | 2.75 |
| Ethyl Alcohol | 3.3 |
| Ethyl Chloride | 3.8 |
| Fuel Oil No. 1 | 0.7 |
| Hydrogen | 4 |
| Isobutane | 1.8 |
| Isopropyl Alcohol | 2 |
| Gasoline | 1.4 |
| Kerosine | 0.7 |
| Methane | 5 |
| Methyl Alcohol | 6.7 |
| Methyl Chloride | 10.7 |
| Methyl Ethyl Ketone | 1.8 |
| Naphthalene | 0.9 |
| n-Heptane | 1.0 |
| n-Hexane | 1.25 |
| n-Pentene | 1.65 |
| Neopentane | 1.38 |
| Neohexane | 1.19 |
| n-Octane | 0.95 |
| iso-Octane | 0.79 |
| n-Pentane | 1.4 |
| iso-Pentane | 1.32 |
| Propane | 2.1 |
| Propylene | 2.0 |
| Silane | 1.5 |
| Styrene | 1.1 |
| Toluene | 1.27 |
| Triptane | 1.08 |
| p-Xylene | 1.0 |

In an embodiment, a detector generates a signal in response to the detector detecting a level of combustible gas of at most 25% of the lower explosive limit of the combustible gas. For example, referring to the chart above it can be seen that methane has a lower explosive limit of 5%. 25% of the lower explosive limit of methane would be 1.25% methane mixed in air. In this embodiment, the detector would not generate a signal that caused the hot work within the enclosure to terminate until the detector detected a concentration of methane in air of 1.25%.

Figure 5:
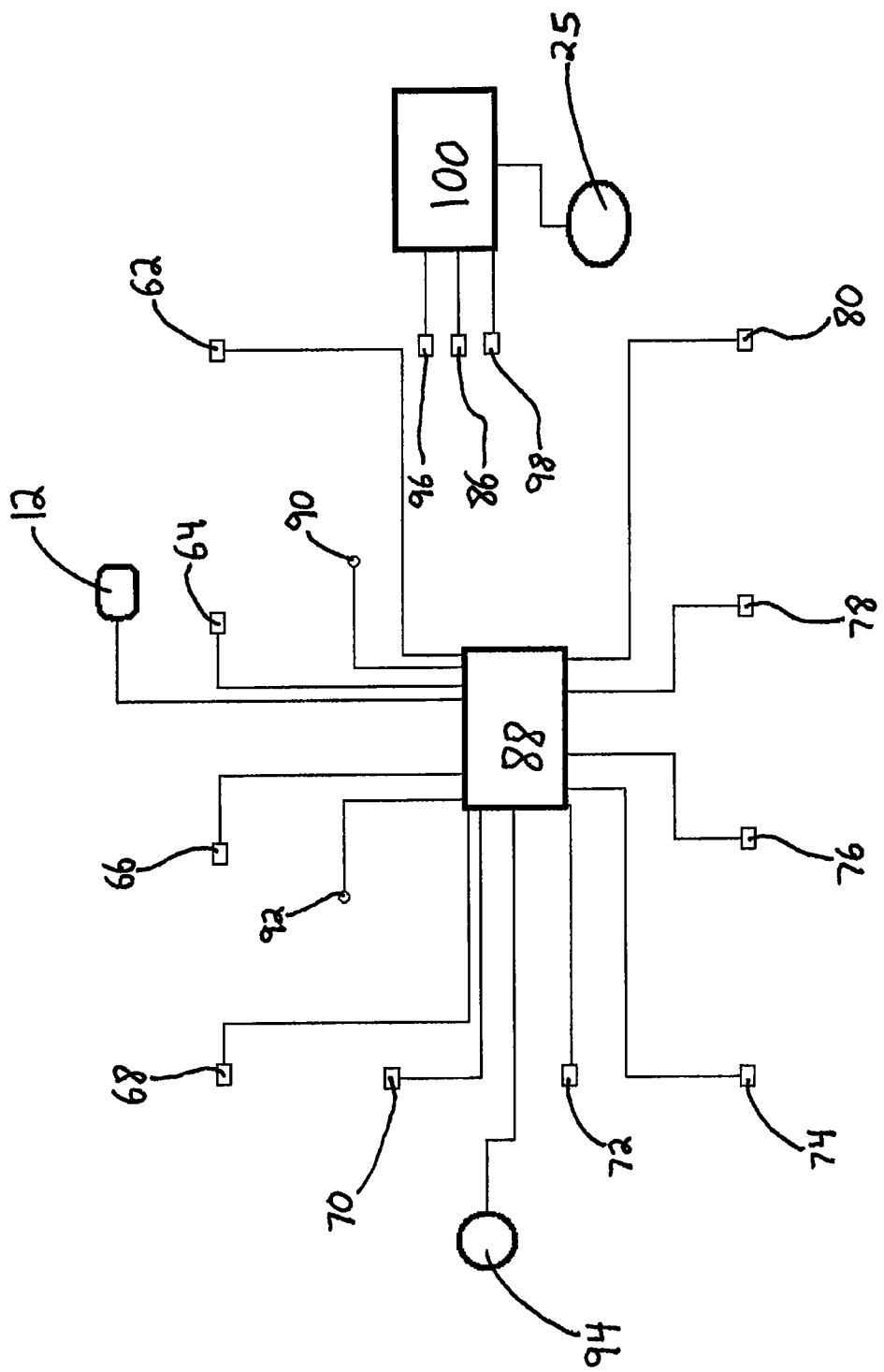
FIG. 5 is a schematic view of an embodiment described herein.
Figure 6:
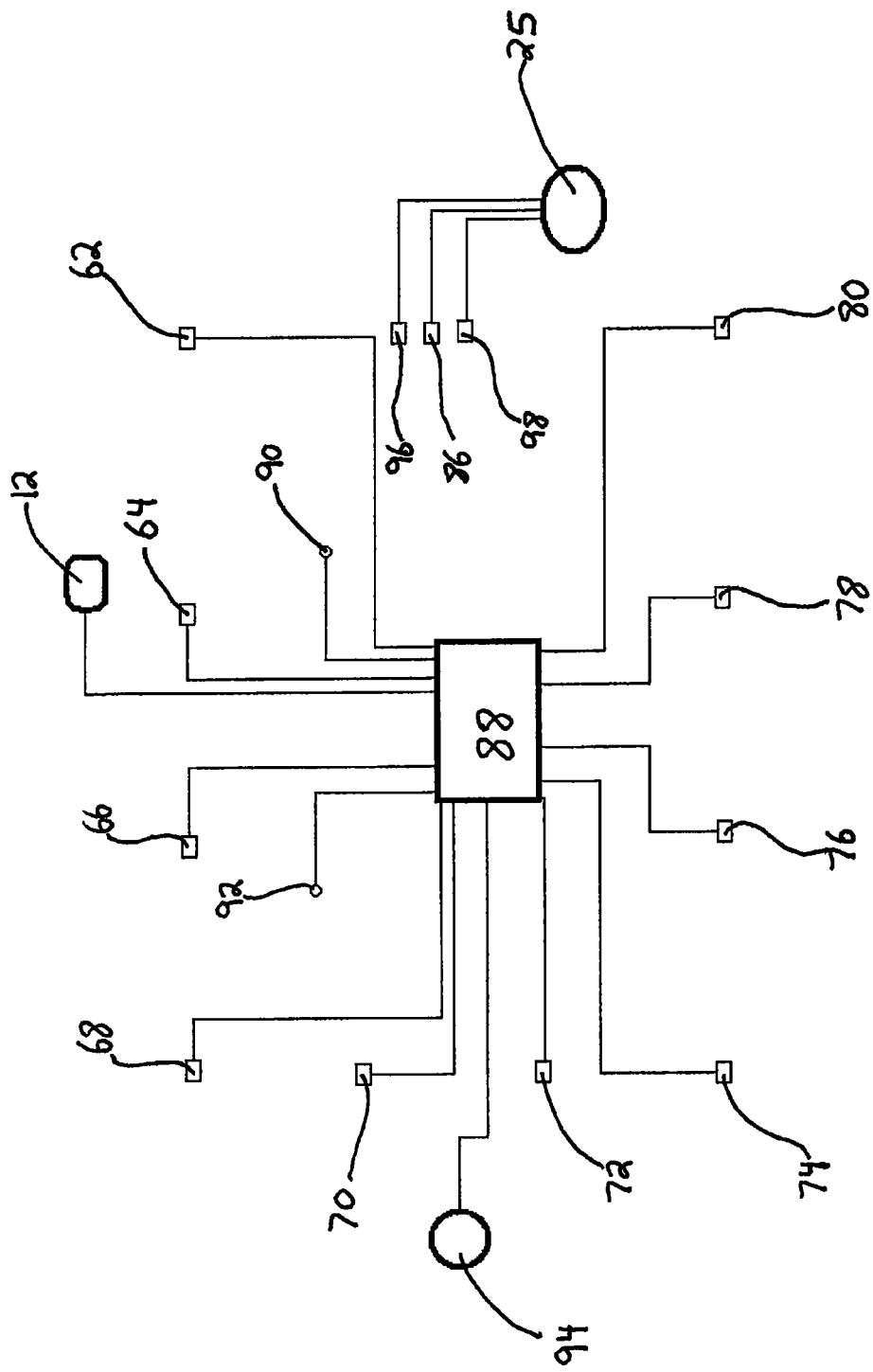
FIG. 6 is a schematic view of an embodiment described herein.

As opposed to, or in addition to, being in communication with the hot work apparatus 12, one or more of detectors 62, 64, 66, 68, 70, 72, 74, 76, 78, 80, 86, 96 and 98, such as combustible gas detector 86, carbon monoxide detector 96 and oxygen detector 98, can be in communication with the blower assembly 25. For example, as shown in FIGS. 5 and 6, detectors 86, 96 and 98 can be isolated from the hot work apparatus 12 and can be in communication with the blower assembly 25, such as the blower 26 and/or a shut off valve of the blower assembly 25 that can be located within duct 28. As the term "isolated" is used herein, a first component, such as detectors 86, 96 and/or 98 is isolated from a second component, such as hot work apparatus 12 and/or a controller (described below) if the first and second component are not directly or indirectly in wired or wireless communication with each other. As used herein, a first component is indirectly in wired or wireless communication with a second component if one or more additional components interconnect the first component and the second component by wired or wireless communication. For example, if a first component is in direct wired communication with a controller, and the controller is in direct wired communication with a second component, then the first and second component are in indirect wired communication with each other. As used herein, wireless communication is defined as communication via electromagnetic radiation, such as radio waves, infrared light and/or any other form of electromagnetic radiation. In response to detecting a level of combustible gas, a level of carbon monoxide and/or a level of oxygen in or near to a source of air transferred from the exterior of the enclosure 10 to the interior 14 of the enclosure 10, detector 86, 96 and/or 98 can generate a signal which causes the transfer of air from the exterior of the enclosure 10 to the interior 14 of the enclosure 10 to be stopped, such as by shutting down the blower 26 of the blower assembly 25 and/or closing the shut off valve of the blower assembly 25 and diverting or blocking the flow of air through duct 28. The transfer of air from the exterior of the enclosure 10 to the interior 14 of the enclosure 10 could, for example, be stopped by transmitting a signal to a switch of the blower assembly 25, such as an interface relay. An example of an interface relay is model number 750XBXH-24D produced by MAGNECRAFT.

One or more of detectors 62, 64, 66, 68, 70, 72, 74, 76, 78, 80, 86, 96 and 98 can be in communication, such as wired or wireless communication, with a controller 88. As shown in the embodiment depicted in FIG. 4, each of the detectors can be in communication with the controller 88. The controller can include devices such as a computer, a programmable logic controller or any other suitable device. An example of a controller is a model number S7200 programmable logic controller produced by SIEMENS. The controller 88 can be located in the interior 14 of the enclosure 10 or can be located exterior of the enclosure 10. In an embodiment, the controller 88 can be attached to housing 38. The controller 88 can receive signals generated by one or more of detectors 62, 64, 66, 68, 70, 72, 74, 76, 78, 80, 86, 96 and 98 in response to the detectors detecting the presence of a condition. The controller can then process the signals received from the detectors and can generate a second signal which is transmitted to the hot work apparatus 12 and terminates the hot work and/or causes the hot work apparatus 12 to shut down. For example, detectors 62, 68 and 74 can generate an input signal in response to detecting the presence of a predetermined condition, such as a predefined level of combustible gas in the air transferred from the interior 14 of the enclosure 10 to the exterior of the enclosure 10. The input signal can be transmitted to the controller 88, which can process the input signal. The controller 88 can then transmit an output signal to the hot work apparatus 12, such as a switch, relay, solenoid valve or other suitable device of the hot work apparatus 12, which terminates the hot work and/or causes the hot work apparatus to shut down; and/or the controller 88 can then transmit an output signal to the blower assembly 25, which causes the transfer of air from the exterior of the enclosure 10 to the interior 14 of the enclosure 10 to be stopped, such as by shutting down the blower 26 of the blower assembly 25 and/or closing the shut off valve of the blower assembly 25. The controller 88 can include a display screen which can display information, such as the status of the detectors or other components that are in communication with the controller 88. The display screen can be within the interior 14 of the enclosure 10, or can be exterior of the enclosure. In an embodiment, a first display screen of the controller 88 can be attached to the housing 38 and a second display screen of the controller 88 can be located within the interior 14 of the enclosure 10. The first and/or second display screen can be in communication, such as by wired or wireless communication, with the controller 88. In an embodiment, the display screen can be a model TP 270 touch screen display produced by SIEMENS.

As shown in FIGS. 5 and 6, detectors 86, 96 and/or 98 can be isolated from controller 88 and the hot work apparatus 12, and can be in communication with the blower assembly 25, such as a switch, relay, solenoid valve or other suitable device of the blower assembly 25. In the embodiment depicted in FIG. 6, detectors 86, 96 and 98 are in direct communication with the blower assembly 25. In the embodiment depicted in FIG. 5, detectors 86, 96 and 98 are in communication with the blower assembly 25 by being in communication with a second controller 100, which is itself in communication with the blower assembly 25. In an embodiment, the second controller 100 can be of a similar or identical type as controller 88. In an embodiment, detecting a condition such as combustible gas, carbon monoxide and/or oxygen entering the enclosure 10 can be accomplished by shutting down the blower assembly 25 in response to one or more of detectors 86, 96 and 98 detecting a condition, and then by detecting the resulting pressure drop in the atmosphere within the enclosure 10 so as to detect a condition entering the enclosure 10.

An alarm 94 such as a visual and/or audio alarm, can also be in communication with the detectors, the controller 88 and/or the second controller 100, and can be triggered in response to a signal received from the detectors, the controller 88 and/or the second controller 100.

Oxygen and/or carbon monoxide detectors 64, 70, and 76 can be in communication with the hot work apparatus 12, the blower assembly 25, the controller 88, the second controller 100 and/or the alarm 94. Additionally, pressure detectors 66, 72, and 78 and/or any other detectors can be in communication with the hot work apparatus 12, the blower assembly 25, the controller 88, the second controller 100 and/or the alarm 94.

An interior manual shut down switch 90 and/or an exterior manual shutdown switch 92 can be connected to the hot work apparatus 12, the blower assembly 25, the controller 88, the second controller 100 and/or the alarm 94. The interior manual shut down switch 90 and/or the exterior manual shutdown switch 92 can be devices such as a switch, button, lever, knob, toggle or any other device that, when triggered, can shut down the hot work apparatus 12, activate the alarm 94 and/or shut down the blower assembly 25. The interior manual shut down switch 90 and/or an exterior manual shutdown switch 92 can be triggered by a user, such as one or more persons designated as a firewatch, who is within the enclosure 10 and/or exterior of the enclosure 10. One or more additional manual shut down switches can be located within the interior of the enclosure 10 and/or exterior to the enclosure 10.

As used herein, the detectors, controller 88, second controller 100, interior manual shut down switch 90 and/or exterior manual shut down switch 92 are in communication with the hot work apparatus 12, the blower assembly 25 and/or the alarm 94 if a signal generated by the detectors, controller 88, second controller 100, interior manual shut down switch 90 and/or exterior manual shut down switch 92 results in terminating the hot work, stopping the transfer of air from the exterior of the enclosure 10 to the interior 14 of the enclosure 10 and/or activates the alarm 94.

In an embodiment, the housing inlet aperture 40 of two or more housings 38 can be placed adjacent to apertures in the sides of the enclosure 10 at various locations. For example, the housing inlet aperture 40 of a first housing 38 can be placed adjacent to an aperture near the ceiling 16 of the enclosure 10, so as to detect combustible gases for example that are lighter than air. The housing inlet aperture 40 of a second housing 38 can be placed adjacent to an aperture near the floor 18 of the enclosure 10, so as to detect combustible gases for example that are heavier than air.

Referring to the embodiments depicted in FIGS. 1 and 3, the distance between the housing 38 and the enclosure 10, such as the distance between the housing inlet aperture 40 and outlet aperture 34, can be a distance that can maintain a positive pressure atmosphere within the enclosure 10 and/or can maintain a positive pressure atmosphere within the housing 38. When air is being transferred from the exterior of the enclosure 10 to the interior 14 of the enclosure 10, such as by blower assembly 25, the pressure level of the positive pressure atmosphere within the enclosure 10 and the housing 38 can be reduced by increasing the distance between the housing 38 and the enclosure 10. The pressure level of the positive pressure atmosphere within the enclosure 10 and the housing 38 can be increased by decreasing the distance between the housing 38 and the enclosure 10. In an embodiment, the distance between the housing 38 and the enclosure 10 can be fractions of a centimeter. The distance between the housing 38 and the enclosure 10 can also be varied as described above so that all or substantially all of the air that enters the housing 38 is air that has been transferred from the interior 14 of the enclosure 10.

In an embodiment, the enclosure 10 can also have an entry way, such as a door, that can allow a person to enter and exit the enclosure 10. The entry way can include an air lock that can allow a person to enter and exit the enclosure 10 with little or no pressure drop in the positive pressure atmosphere within the enclosure 10. The air lock can be a separate chamber from the enclosure 10 and can have a conduit interconnecting the interior 14 of the enclosure 10 and the interior of the air lock. The conduit can have a valve that can be opened or closed to allow the pressure differential between the interior 14 of the enclosure 10 and the interior of the air lock to be equalized. In an embodiment, blower assembly 25 can be in fluid communication with the interior of the air lock, such as by a second duct, and can create a positive pressure atmosphere within the air lock. In an embodiment, a second blower assembly can be in fluid communication with the interior of the air lock, and can create a positive pressure atmosphere within the air lock. When a person enters the air lock from the exterior of enclosure 10 and closes an exterior door of the air lock, a short period of time will elapse while the pressure in the air lock increases to a pressure level equal to or greater than the pressure level inside of the enclosure 10. Once this condition occurs, the person can then open the door to enclosure 10 and enter enclosure 10 without causing a pressure drop within enclosure 10, thereby causing a spurious shut down of hot work within the enclosure 10. Likewise, a person exiting enclosure 10 can enter the air lock and close the door to the enclosure 10 before opening the exterior door of the air lock to exit the air lock, thereby preventing a spurious shutdown of hot work operations. In an embodiment, pressure detectors can detect the level of pressure within the air lock and can allow for the pressure differential between the interior of the air lock and the interior 14 of the enclosure 10 to be determined and/or displayed to a person entering or exiting the enclosure 10.

In operation of an embodiment, enclosure 10 can be formed at a location where hot work will be conducted within the enclosure 10. Blower assembly 25 can be activated to transfer air from the exterior of the enclosure 10 to the interior 14 of the enclosure 10 and produce a positive pressure atmosphere within the enclosure 10. Once a positive pressure atmosphere is produced within the enclosure 10, hot work can be conducted within the enclosure 10. The positive pressure atmosphere within the enclosure can cause air to be transferred from the interior 14 of the enclosure 10 to the exterior of the enclosure, and into the interior 42 of housing 38. The air transferred from the interior 14 of the enclosure 10 to the interior 42 of the housing 38 can then be sampled by detectors 62, 64, 66, 68, 70 and/or 72 for the presence of a condition, such as a level of combustible gas, oxygen and/or pressure. The positive pressure atmosphere within the housing 38 can then cause the air to be transferred from the interior 42 of the housing 38 to the exterior of the housing 38 through damper 54. If detectors 62, 64, 66, 68, 70, 72, 74, 76, 78, 80, 86, 96 and/or 98 detects the presence of a condition, one or more of the detectors can generate a signal which results in hot work within the enclosure 10 and/or the transfer of air from the exterior of the enclosure 10 to the interior 14 of the enclosure being automatically terminated. A person can then view a display screen of the controller 88 to determine the cause of the automatic shut down. Once the cause of the automatic shut down has been determined and remedied, the above process can be repeated.

In an embodiment, a first person, such as a firewatch, can be outside of the enclosure 10 and can have fire-fighting equipment, a radio and a combustible gas detector. The first person can monitor the enclosure and/or other components described herein for at least half an hour prior to, during and at least half an hour after hot work is conducted within the enclosure 10. The first person can also terminate the hot work within the enclosure 10 by activating the exterior manual shut down switch 92. In an embodiment, the hot work can be conducted on a production platform, and the first person can be in close proximity to an emergency shut down station of the production platform. The first person can activate the emergency shut down station, which can terminate operations on the production platform as well as terminate the hot work within the enclosure 10. A second person, such as a firewatch, can be inside of the enclosure 10 and can monitor the level of combustible gas, the level of oxygen and/or other gases within the enclosure 10. The second person can terminate the hot work within the enclosure 10 by activating the interior manual shut down switch 90. Lights and a radio can be located within the enclosure 10 and can have an independent power source that allows the lights and radio to function even if power to the enclosure 10 is shut down. A fire extinguisher, such as a 30 pound (13.61 kilogram) fire extinguisher, can also be located within the enclosure 10. Prior to conducting hot work within the enclosure 10, the detectors can be calibrated and/or drills can be conducted to determine whether the methods and apparatuses described herein are functioning properly.

Figure 4:
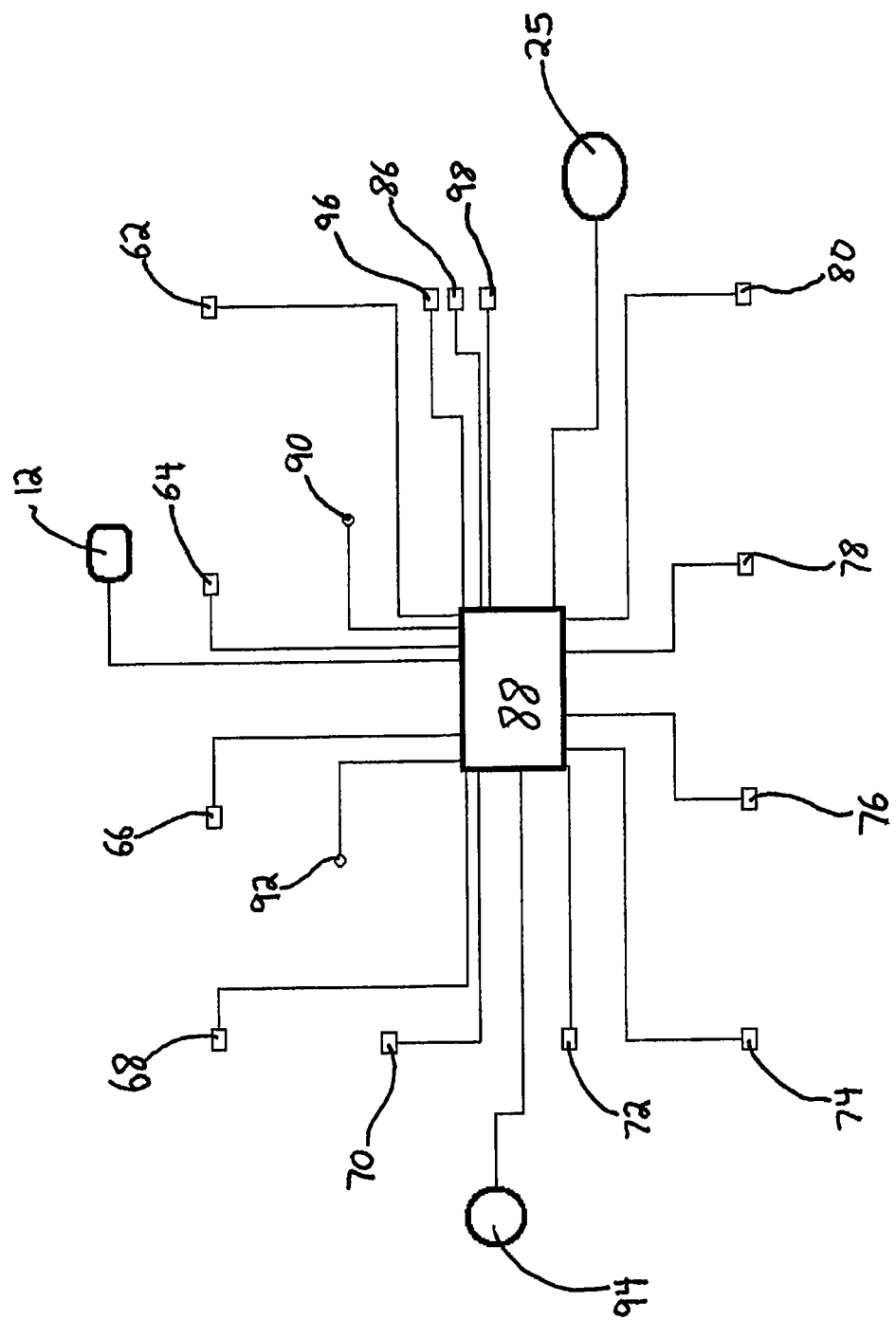
FIG. 4 is a schematic view of an embodiment described herein.

Referring to FIG. 4, combustible gas detector 86, carbon monoxide detector 96, oxygen detector 98 and blower assembly 25 are in communication with controller 88. In response to one or more of detectors 86, 96 and 98 detecting a condition, such as detector 86 detecting a level of combustible gas in or near to a source of air being transferred from the exterior of the enclosure to the interior of the enclosure by blower assembly 25, combustible gas detector 86 can generate a signal which is transmitted to controller 88. The controller 88 can then stop the transfer of air from the exterior of the enclosure to the interior of the enclosure, such as by sending a signal to blower assembly 25 which causes the blower assembly 25 to shut down. As opposed to each of detectors 62, 64, 66, 68, 70, 72, 74, 76, 78, 80, 86, 96 and/or 98 being in communication with the controller 88 (as shown in FIG. 4), one or more of the detectors can be isolated from the controller 88, and can be in communication with the hot work apparatus 12, the blower assembly 25, the second controller 100 and/or the alarm 94.

An embodiment is a method of detecting a condition such as a combustible gas entering the enclosure 10 by detecting a pressure drop in the atmosphere within the enclosure 10. Referring now to FIGS. 5 and 6, combustible gas detector 86, carbon monoxide detector 96 and oxygen detector 98 are in communication with blower assembly 25. The detectors 86, 96 and 98, and the blower assembly 25 are isolated from the controller 88 and the hot work apparatus 12. As shown in FIGS. 5 and 6, pressure detectors 66, 72 and 78 are in communication with the controller 88. Referring now to FIGS. 1, 2 and 3, in an embodiment, detecting a condition such as a combustible gas entering the enclosure 10 by detecting a pressure drop in the atmosphere within the enclosure 10 can be accomplished by: transferring air from the exterior of the enclosure 10 to the interior 14 of the enclosure 10, such as by blower assembly 25; detecting a level of combustible gas in or near to a source of the air transferred from the exterior of the enclosure 10 to the interior 14 of the enclosure 10, such as by combustible gas detector 86; stopping the transferring of air from the exterior of the enclosure 10 to the interior 14 of the enclosure 10 in response to the detecting a level of combustible gas, such as by combustible gas detector 86 generating a signal which results in blower assembly 25 shutting down; and detecting a pressure drop in the atmosphere within the enclosure 10 so as to detect a combustible gas entering the enclosure 10, such as by pressure detectors 66, 72 and/or 78. Since detecting a pressure drop in the atmosphere within the enclosure 10 can indicate that a combustible gas is entering the enclosure 10, the above method can allow for the detection a combustible gas entering the enclosure 10 by detecting a pressure drop in the atmosphere within the enclosure 10. In an embodiment, in response to detecting a pressure drop in the atmosphere within the enclosure 10, one or more of the pressure detectors can send a signal to the controller 88. In response to receiving the signal from one or more of the pressure detectors, the controller 88 can indicate that combustible gas was detected entering the enclosure 10 by displaying a message on a display screen of the controller 88. In an embodiment, the entry way of the enclosure 10 can include an air lock, such as the air lock described above, that can reduce or eliminate the chance that the controller 88 incorrectly indicates that combustible gas was detected entering the enclosure 10. Further, hot work being conducted within the enclosure 10 can be terminated in response to the detecting a pressure drop in the atmosphere within the enclosure 10, such as by one or more of the pressure detectors generating a signal that results in the hot work being terminated. Although the above method can allow for the detection of a condition, such as a combustible gas, entering the enclosure 10 by detecting a pressure drop in the atmosphere within the enclosure 10, a pressure drop in the atmosphere within the enclosure 10 can also be caused by circumstances other than detection of a condition entering the enclosure. For example, the blower assembly 25 could malfunction and shut down, or an opening could be formed in the sides of the enclosure 10 that caused the interior 14 of the enclosure 10 to depressurize; in such a circumstance detecting a pressure drop in the atmosphere within the enclosure 10 would not be detecting a condition entering the enclosure 10.

The embodiments shown in the drawings and described above are exemplary of numerous embodiments that may be made within the scope of the appended claims. It is contemplated that numerous other configurations may be used, and the material of each component may be selected from numerous materials other than those specifically disclosed. In short, it is the applicant's intention that the scope of the patent issuing herefrom will be limited only by the scope of the appended claims.

We claim:

1. A method of detecting a combustible gas entering an enclosure by detecting a pressure drop in the atmosphere within the enclosure comprising:
   a. transferring air from an exterior of the enclosure to an interior of the enclosure;
   b. detecting a level of combustible gas in or near to a source of the air transferred from the exterior of the enclosure to the interior of the enclosure;
   c. stopping said transferring of air from the exterior of the enclosure to the interior of the enclosure in response to said detecting a level of combustible gas; and
   d. detecting a pressure drop in the atmosphere within the enclosure so as to detect a combustible gas entering the enclosure.

2. The method of claim 1 further comprising conducting hot work in the enclosure.

3. The method of claim 2 further comprising terminating the hot work in the enclosure in response to said detecting a pressure drop in the atmosphere within the enclosure.

4. The method of claim 3 further comprising transmitting a signal to a controller in response to said detecting a pressure drop in the atmosphere within the enclosure.

5. The method of claim 4 further comprising transmitting a signal from a controller to a power source of the hot work.

6. The method of claim 4 wherein said terminating the hot work further comprises terminating the hot work in response to a signal from the controller.

* * * * *